(12) United States Patent
Sund et al.

(10) Patent No.: US 11,291,578 B2
(45) Date of Patent: Apr. 5, 2022

(54) ADHESIVE WAFER WITH AN INTEGRATED RELEASE LAYER

(71) Applicant: Coloplast A/S, Humlebaek (DK)

(72) Inventors: Anders Grove Sund, Alleroed (DK); Esben Stroebech, Hoersholm (DK); Philip Holler Langhorn, Hilleroed (DK); Carsten Sletten, Espergaerde (DK); Michael Hoejstroem, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 315 days.

(21) Appl. No.: 16/486,499

(22) PCT Filed: Feb. 20, 2018

(86) PCT No.: PCT/DK2018/050034
§ 371 (c)(1),
(2) Date: Aug. 16, 2019

(87) PCT Pub. No.: WO2018/149463
PCT Pub. Date: Aug. 23, 2018

(65) Prior Publication Data
US 2021/0275342 A1     Sep. 9, 2021

(30) Foreign Application Priority Data
Feb. 20, 2017 (DK) .............. PA 2017 70117

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC ................ A61F 5/4404; A61F 5/443
See application file for complete search history.

(56) References Cited

U.S. PATENT DOCUMENTS

| | | | |
|---|---|---|---|
| 3,908,658 A * | 9/1975 | Marsan | A61F 5/443 604/336 |
| RE29,453 E | 10/1977 | Weddle | |
| 5,496,296 A | 3/1996 | Holmberg | |
| 5,714,225 A | 2/1998 | Hansen et al. | |
| 6,312,415 B1 | 11/2001 | Nielsen et al. | |
| 6,387,082 B1 | 5/2002 | Freeman | |
| 6,764,474 B2 | 7/2004 | Nielsen et al. | |
| 7,862,878 B2 | 1/2011 | Stroebech et al. | |
| 9,271,863 B2 | 3/2016 | Stroebech et al. | |

(Continued)

FOREIGN PATENT DOCUMENTS

| | | |
|---|---|---|
| CA | 2486485 A1 | 5/2006 |
| CN | 102413797 A | 4/2012 |

(Continued)

*Primary Examiner* — Tatyana Zalukaeva
*Assistant Examiner* — Hans Kaliher
(74) *Attorney, Agent, or Firm* — Coloplast Corp., Coloplast A/S; Nick Baumann

(57) ABSTRACT

An adhesive wafer for an ostomy device, the wafer comprising a first adhesive layer, a backing layer on the distal side of the first adhesive layer, a second skin facing adhesive layer and a hole for accommodating a stoma. Embedded between the adhesive layers is a release layer capable of releasing a neutralizing compound to the peristomal skin.

18 Claims, 2 Drawing Sheets

(56) References Cited

U.S. PATENT DOCUMENTS

| | | |
|---|---|---|
| 2005/0096611 A1 | 5/2005 | Stoyer et al. |
| 2006/0058577 A1* | 3/2006 | Davies .................... A61F 5/445 600/32 |
| 2009/0010998 A1 | 1/2009 | Marchitto et al. |
| 2012/0041404 A1 | 2/2012 | Bach et al. |
| 2012/0220965 A1* | 8/2012 | Ramjit .................... A61F 5/443 604/336 |
| 2013/0072885 A1 | 3/2013 | Luther et al. |
| 2013/0096522 A1 | 4/2013 | Svensby et al. |
| 2013/0226117 A1 | 8/2013 | Hansen et al. |
| 2013/0304008 A1 | 11/2013 | Hanuka et al. |
| 2014/0221950 A1 | 8/2014 | Chang et al. |
| 2014/0316360 A1 | 10/2014 | Ekfeldt et al. |
| 2015/0065971 A1 | 3/2015 | Goldsmith |
| 2016/0143768 A1 | 5/2016 | Stroebech et al. |
| 2016/0151197 A1 | 6/2016 | Johnsen |
| 2018/0104089 A1* | 4/2018 | Nyberg .................... A61F 5/445 |
| 2018/0116859 A1* | 5/2018 | Strobech .................. A61F 5/445 |
| 2018/0296384 A1* | 10/2018 | O'Brien .................... A61F 5/445 |
| 2020/0015996 A1* | 1/2020 | Schertiger ............ A61F 5/4401 |

FOREIGN PATENT DOCUMENTS

| | | | |
|---|---|---|---|
| CN | 102753122 A | 10/2012 | |
| CN | 103153242 A | 6/2013 | |
| CN | 105555236 A | 5/2016 | |
| CN | 105848613 A | 8/2016 | |
| EP | 0686381 A1 * | 12/1995 | ............. A61F 5/443 |
| EP | 0686381 A1 | 12/1995 | |
| EP | 3056225 A1 | 8/2016 | |
| RU | 2118145 C1 | 8/1998 | |
| RU | 2575548 C2 | 2/2016 | |
| RU | 2582426 C2 | 4/2016 | |
| WO | 9855057 A1 | 12/1998 | |
| WO | 2007140785 A1 | 12/2007 | |
| WO | 2010060116 A1 | 5/2010 | |
| WO | 2013055434 A1 | 4/2013 | |
| WO | 2015012953 A1 | 1/2015 | |
| WO | 2016162038 A1 | 10/2016 | |
| WO | 2017059868 A1 | 4/2017 | |

* cited by examiner

ADHESIVE WAFER WITH AN INTEGRATED RELEASE LAYER

The invention relates to an adhesive wafer for an ostomy appliance.

SUMMARY OF THE INVENTION

One aspect of the disclosure provides an adhesive wafer in accordance with the appended claim 1.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION

Figure 1:
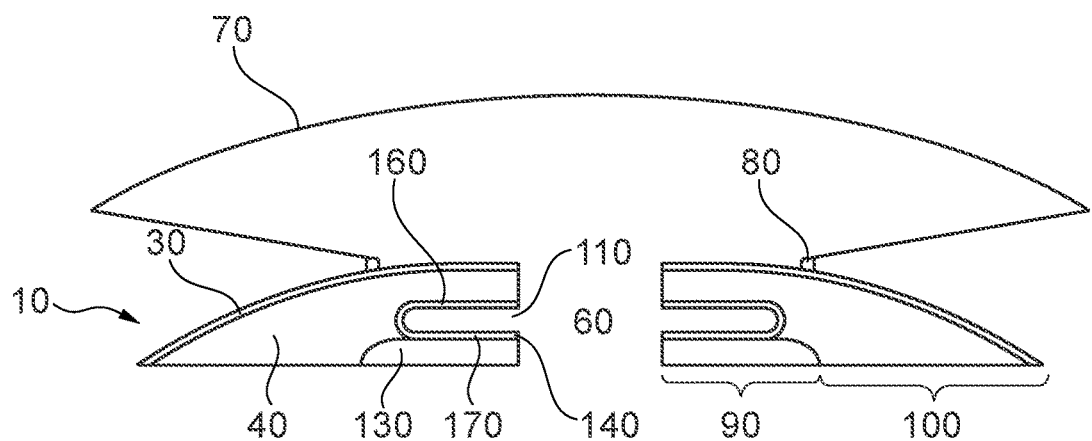
FIG. 1 illustrates a schematic cross-section view of one embodiment of a wafer.

In the following, whenever referring to proximal side of a device or part of a device, the referral is to the skin-facing side, when the wafer or ostomy appliance is worn by a user. Likewise, whenever referring to the distal side of a device or part of a device, the referral is to the side facing away from the skin, when the wafer or ostomy appliance is worn by a user. In other words, the proximal side is the side closest to the user, when the wafer is fitted on a user and the distal side is the opposite side—the side furthest away from the user during use.

An axial direction is defined as the direction of the stoma, when the appliance is worn by a user. Thus, the axial direction is substantially perpendicular to a skin surface of a user, such as an abdominal skin surface. A radial direction is defined as transverse to the axial direction.

In the following, the words 'ostomy' and 'stoma' are used interchangeably without any intention to have different meanings.

By output is herein meant the effluent from a stoma, being faeces and/or urine in a more or less viscous form or mucins secreted from the epithelial layer of the alimentary canal. In the case of a colostomy, the output may be quite solid, whereas an ileostomy may produce more liquid output. The output may contain digestive fluids with enzymes and other components that may be aggressive to the skin and thus may cause maceration and contact dermatitis of the skin if brought into contact with it as well as the output may comprise components that may attack and degrade the adhesive.

Embodiments provide an adhesive wafer for an ostomy device, the wafer comprising a central portion and a peripheral portion, the wafer comprising a first adhesive layer, a backing layer on the distal side of the first adhesive layer, a second skin-facing adhesive layer and a hole for accommodating a stoma, and a release layer configured to releasing a neutralizer, the release layer adapted to be releasable from at least one envelope located between the first and the second adhesive layer.

In embodiments, a portion of the envelope is extending to the edge of the hole.

The wafer may be a part of an ostomy appliance comprising an adhesive wafer and a collecting bag. The collecting bag may be detachably or permanently attached to the wafer along a connection zone circumferencing the hole in a radial distance and having an inlet corresponding with the hole in the wafer.

The wafer comprises a central portion, defined as the area extending radially from the edge of the hole to the connection zone and a peripheral portion, defined as the area extending radially from the connection zone to the outer edge of the wafer.

When an ostomy wafer is applied to the skin surrounding a stoma, the adhesive provides a tight fit to the skin, in order to avoid the output to leak under the wafer and damage the skin and degrade the adhesive. Any output creeping under the wafer is to be avoided as much as possible as it may lead to maceration of the skin as well as degradation of the adhesive, resulting in leakage, unintended detachment of the wafer and discomfort for the user.

When fitting a hole of an ostomy wafer to the area around a stoma, there will be a gap between the edge of the hole in the adhesive plate and the site stoma. The stoma needs room to work due to inter alia peristaltic movements of the intestine; it enlarges when delivering output and shortens when not. In this gap, also called the peristomal gap, output from the stoma may enter and over time degrade the adhesive layer as well as cause skin maceration. By providing a wafer capable of releasing a neutralizer into the gap, the skin and the adhesive at the peristomal gap will be protected. Some of the neutralizer may be flushed into the bag by the output, but most of the neutralizer will stay at the peristomal gap and interact with the output to neutralize its harmful components.

The output from the stoma may flow substantially continuously or it may enter the bag in bursts, e.g. depending on the type of stoma. When the user of the bag is in an upright position, continuous output may flow downwards due to gravity and primarily contact and wet the part of the central portion of the wafer being below the stoma. At the same time, some of the output will flow into the peristomal gap and distribute in the gap around the stoma. However, coming in bursts, and inside a bag and with the distal wall of the bag close to the stoma, the output may spread all over the central portion of the backing layer, including also the area above the stoma. A user wearing a bag, with clothing potentially pushing the bag towards the stoma, a burst of output may for a period fill a volume defined by the wafer, the distal wall and the coupling means. Thus, the output may not immediately flow in the direction of gravity, but will also wet the area of the bag being above the stoma receiving hole and also the entire peristomal gap.

Embodiments provide an ostomy appliance comprising a collecting bag and an adhesive wafer, the wafer comprising a central portion and a peripheral portion, the wafer comprising a first adhesive layer, a backing layer on the distal side of the first adhesive layer, a second skin-facing adhesive layer and a hole for accommodating a stoma, and a release layer configured to releasing a neutralizer, the release layer adapted to be releasable from at least one envelope located between the first and the second adhesive layer.

In embodiments, a portion of the envelope is extending to the edge of the hole.

The wafer is provided with a through-going hole in the central portion. In embodiments, the hole can be adapted in size by cutting to tailor fit the hole in the wafer to an individual stoma.

The envelope containing the release layer is provided between the first adhesive layer and the second adhesive layer. Optionally, at least a part of the envelope is extending to the edge of the hole. When output is entering the peristomal gap between the hole and the stoma it may be brought into contact with the release layer and the neutralizer is released into the gap and neutralizes the output there, decreasing the risk of damaging the skin.

In embodiments, the envelope constitutes a part of the edge portion of the hole. The release layer may be accessed by the output by direct contact at the edge of the hole or the output or moisture therefrom may be transported into the release layer e.g. by a wicking layer in the envelope. In embodiments, the release layer is exposed at the edge portion of the hole, enabling direct contact between the release layer and output from the stoma or moisture.

In embodiments, the envelope may be in the form of a disc circumferending the hole. In embodiments, the envelope may be in the form of a part of a disc or other configurations only partly circumferending the hole.

In embodiments, the envelope is configured to cover the central portion of the wafer. In embodiments, the envelope is extending over a portion of the central portion next to the hole.

In embodiments, the wafer comprises two or more separate envelopes. In embodiments, each envelope is having a portion extending to the edge of the hole.

In embodiments, when cutting the hole, the envelope is cut too and the release layer is arranged in such a way that when cutting the hole larger, a part of the envelope will still constitute a part of the edge of the hole. When output from the stoma is contacting the release layer, it may release the neutralizer into the peristomal gap between the edge of the hole and the stoma.

In embodiments, the envelope is provided with a cover layer. The cover layer may comprise a distal upper layer (separating the release layer from the first adhesive) and a proximal lower layer (separating the release layer from the second adhesive), the upper and the lower layer being sealed together along the edge to constitute an envelope containing the release layer. In embodiments, the envelope is open and unsealed at the portion extending to the edge of the hole. In embodiments, a portion of the release layer next to the edge of the hole is uncovered by the cover layer enabling the release layer being directly accessible from the edge of the hole.

In embodiments, the cover layer is covering the surface of the release layer facing the first and the second adhesive layers. The cover layer may prevent direct contact between the adhesive layers and the release layer and thereby protect the adhesives from any interference with the release layer or moisture coming from the release layer.

In embodiments, the upper layer and the lower layer of the cover layer are connected at connection points. The connection points may be distributed homogeneously over the envelope or they may be arranged in a pattern. The connection points ensure that the release layer is substantially form stable even when the release layer may be wetted, swelled or eroded. In embodiments, the connection points may be in the form of zones where the upper and the lower film is connected, thereby providing separate envelopes. The zones may be in the form of lines, dots or areas. In embodiments, the connection points are radial lines. In embodiments, the connection points are areas dividing the envelope into separate envelopes. The first adhesive layer and backing layer may separate and move away from the second adhesive layer when the release layer is eroded away, this is avoided when the connection points are present in the cover layer.

In embodiments, the cover layer is impermeable to moisture. The cover layer may prevent moisture from the release layer from entering the adhesive layers. In embodiments, the upper layer and the lower layer of the cover layer have different properties, for example with regard to flexibility and plasticity. This provides more control with swelling of the release layer.

In embodiments, the cover layer may be in the form of a coating. Such coating may be a powder coating or a solid coating. In embodiments, the cover layer is a water-soluble film that slowly dissolves when exposed to moisture.

In embodiments, the release layer comprises a matrix with a neutralizer incorporated therein. The matrix serves as a carrier of the neutralizer and is capable of releasing of the neutralizer.

By neutralizer is herein meant a neutralizing substance capable of neutralizing or at least minimizing the level of skin- or adhesive-aggressiveness of the output.

In embodiments, the neutralizer comprises a clay, such as organophilic clay, for example bentonite or synthetic clay such as laponite. Examples of such clays are disclosed in EP 1 140 009. In embodiments, the neutralizer may be potato-derived inhibitors or protease inhibitors. Examples of potato-derived inhibitors such as potato protein are disclosed in EP 1 736 136.

In embodiments, the matrix is a composition in which the neutralizer is incorporated. The neutralizer may be dissolved in the matrix or it may be dispersed as particles in the matrix.

In embodiments, the release layer may be in the form of coated neutralizer particles.

In embodiments, the matrix of the release layer is designed to release neutralizer when the release layer is exposed to certain conditions. Such conditions may for example be in the presence of output from the stoma or in the presence of moisture. In embodiments, the matrix is dissolved or disintegrated by contact to the output from the stoma, thereby releasing the neutralizer.

Inside a collecting bag, the humidity will quickly reach about 100% humidity, so the presence of moisture in the bag is substantial. In embodiments, where the matrix is sensitive to moisture, the release of neutralizer from the neutralizer matrix may initiate shortly after applying the wafer.

In embodiments, the matrix is in the form of a gel, foam, film layer, paper or a coating. Such coating may for example be solid or powder coating. In embodiments, the matrix and the neutralizer form a colloidal solution such as a sol.

In embodiments, a matrix is in the form of a water-soluble film such as a polyvinyl alcohol film, for example a Monosol 7031 film.

In embodiments, the matrix is soluble in water or a component of the output. It may be slowly soluble, by slowly is herein meant that the matrix layer will not be washed away instantly, but will slowly dissolve and provide a steady release of neutralizer over time, for example during wear time of the wafer. In embodiments, the matrix is swelling during absorption of moisture.

In embodiments, the matrix may absorb moisture and turn into a gel like material when wetted. The matrix may be delivered in dry form and swell into a gel when brought into contact with moisture. In embodiments, the matrix is delivered as a gel. The gel may be slowly soluble in water or in a component of the output or it may be insoluble but able to release the neutralizer when exposed to stomal output or moisture. In embodiments, the matrix is a material capable of forming a gel when wetted or it may be in the form of a gel.

Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine.

In embodiments, the matrix comprises water-soluble or water swellable polysaccharides and/or hydrocolloids. The polysaccharides or hydrocolloids may dissolve or hydrate when exposed to moisture from the output, thereby releasing neutralizer.

In embodiments, the matrix comprises protein. In embodiments, the matrix comprises gelatine.

In embodiments, the matrix is substantially non-adhesive. By non-adhesive is meant that it is not adhesive, though it may under certain circumstances become slightly sticky.

The collecting bag usually comprises a front wall on the distal side and a rear wall on the proximal side. The walls may be made of gas- and liquid impermeable foil-material (for example of polyethylene (PE), polyvinyl-chloride (PVC) or ethylene-vinyl-acetate (EVA)) that is welded around the edges or the rim, so as to form a pouch defining a waste collecting chamber. The bag may be welded only partly around the rim so that an opening for emptying the bag is provided at the bottom of the bag. In that case, the bag may be provided with means for closing that opening. The waste inlet opening is provided in the rear wall and placed in the upper part of the collecting bag, so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

In embodiments, the backing layer of the adhesive wafer is gas and water impermeable.

In embodiments, the first adhesive layer and the second adhesive layer may be two different adhesives with different properties. In embodiments, the first and the second adhesive may be the same adhesive.

In embodiments, the first adhesive layer covers the entire proximal surface of the backing layer. In embodiments, the second adhesive layer covers at least the central portion of the wafer. In embodiments, the second adhesive layer is larger than the envelope such that the envelope will be enclosed between the first and the second adhesive.

Prior to application to the skin a protective release liner may cover the skin contacting side of a pressure sensitive adhesive layer, in order to ensure that the properties of the adhesive are preserved and that the adhesive surface is not laid open until just before use. The release liner may suitably be a siliconised or fluorinated release liner, such as a siliconised or fluorinated craft paper, polyethylene, polypropylene or polyethylene terephthalate film. Suitably, the release liner is a siliconised polyethylene film, such as medium density polyethylene film from the company Huhtamaki.

Disclosed is a method of protecting the peristomal skin of a user, the method comprising the following steps: providing an ostomy appliance comprising a collecting bag and an adhesive wafer, the wafer comprising a central portion and a peripheral portion, the wafer comprising a first adhesive layer, a backing layer on the distal side of the first adhesive layer, a second skin-facing adhesive layer and a hole for accommodating a stoma, and a release layer, the release layer adapted to be releasable from at least one envelope located between the first and the second adhesive; optionally adapting the size of the hole to fit a stoma; and attaching the wafer to the skin around a stoma. The output from the stoma may flow into the gap between the hole and the stoma, contact the release layer and thereby releasing the neutralizer into the peristomal gap.

Embodiments, and features of the various exemplary embodiments described in this application, may be combined with each other ("mixed and matched"), unless specifically noted otherwise.

DETAILED DESCRIPTION OF THE DRAWING

In the following detailed description, reference is made to the accompanying drawings. The drawings form a part of this specification and illustrate exemplary embodiments for practicing the invention. Directional terminology, such as "top," "bottom," "front," "back," etc., is used with reference to the orientation of the figures being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Initially, it shall be noted that the figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

In FIG. 1 is shown a cross-sectional view of an ostomy appliance. The appliance comprises an adhesive wafer 10 having a first layer of adhesive 40 facing a backing layer 30 covering the distal surface of the first adhesive 40. The wafer 10 comprises a central portion 90, defined as the area extending radially from the edge of the hole 60 to the connection zone 80 and a peripheral portion 100, defined as the area extending radially from the connection zone 80 to the outer edge of the wafer 10. A central hole 60 is provided in the wafer to accommodate a stoma 20. The size of the hole 60 may be adapted by cutting to tailor fit the hole 60 to the anatomy of the stoma 20. The wafer is provided with a collecting bag 70, the bag being connected to the wafer along a connection zone 80 circumferencing the hole 60 in a radial distance. The bag 70 may be detachably connected to the wafer 10 in a way so that the bag 70 may be detached from the wafer 10 and exchanged, or the bag 70 may be inseparately connected to the wafer 10 for example by welding. A second skin-facing adhesive layer 130 is provided over at least at the central portion of the wafer. A release layer 110 is located between the first adhesive layer 40 and the second adhesive layer 130 and at least a part of the release layer 110 is extending to the edge of the central hole 60. The release layer 110 may be in the form of a disc essentially extending over the central portion 90 of the wafer. The release layer 110 is encapsulated in a cover layer 140, covering the entire surface of the release layer 110 except from the part next to the hole 60 and defining an envelope containing the release layer 110. The cover layer 140 comprises an upper layer 160 facing the first adhesive layer 40 and a lower layer 170 facing the second adhesive layer 130. The cover layer 140 prevents direct contact between the first and the second adhesive layers 40, 130 and the release layer 110.

Figure 2:
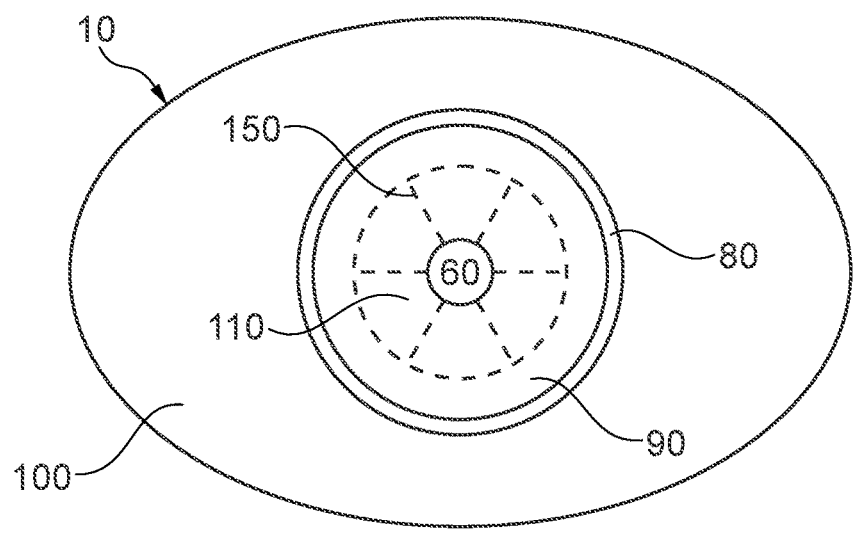
FIG. 2 illustrates a plan view of an embodiment of a wafer.

FIG. 2 shows an embodiment of an adhesive wafer 10 seen from the distal side, with a central portion 90 surrounding a hole 60 for accommodating a stoma 20, and a peripheral portion 100 circumferencing the central portion 90. Along the transition between the central portion 90 and the peripheral portion 100 is the connection zone 80. The connection zone 80 may be in the form of a coupling for attaching a collecting bag (not shown). A release layer 110 is provided at the central portion of the wafer, the location of the release layer 110 is here indicated by broken lines as the release layer is integrated in the wafer by being embedded in the adhesive. The release layer 110 is in the form of a disc and extending over a part of the central portion 90, and at least being present at the edge portion of the hole 60. The cover layer 140 may be provided with connection points, here in the form of radial lines 150, at these connection points 150 the upper and the lower layers 160, 170 of the cover layer 140 are connected, for example by welding. The connection points 150 serve as stabilizing structure in order to avoid the adhesive layers 40, 130 to drift apart when the release layer 110 is swelling or eroded.

Figure 3:
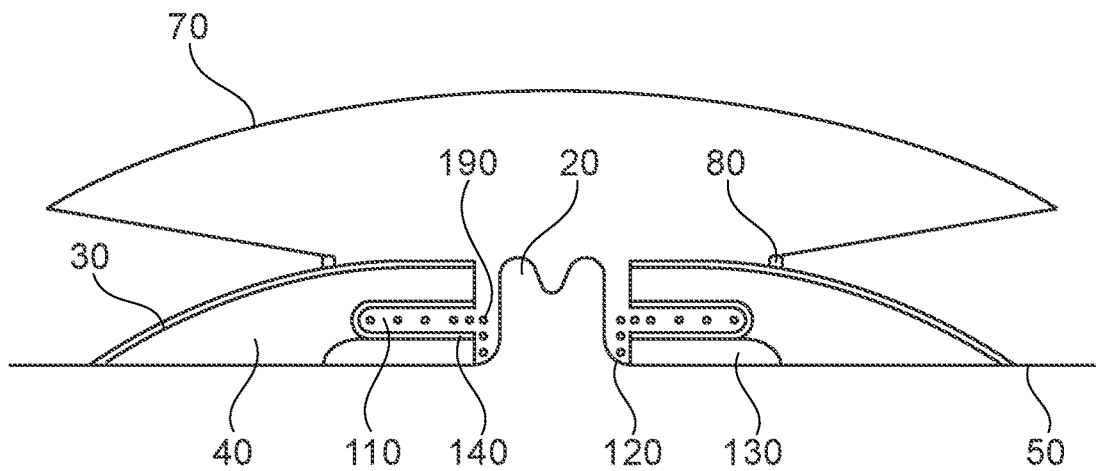
FIG. 3 illustrates a schematic cross-section view of an embodiment of a wafer in use.

FIG. 3 shows an embodiment in use, the wafer 10 being arranged around a stoma 20 and the effluent from the stoma flowing into the peristomal gap 120 between the stoma and the edge of the hole 60 in the wafer, thereby contacting the release layer 110 and facilitate the neutralizer 190 to be released and flow into the peristomal gap 120 where it may protect the skin from the aggressive output.

Figure 4:
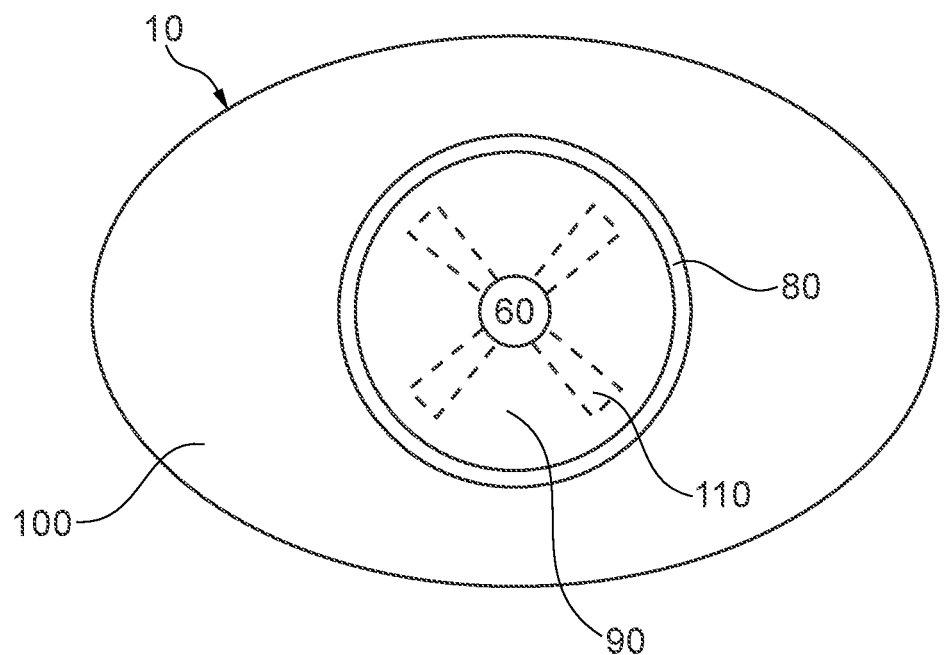
FIG. 4 illustrates a plan view of an embodiment of a wafer with multiple envelopes.

FIG. 4 shows an embodiment of an adhesive wafer 10 seen from the distal side, with a central portion 90 surrounding a hole 60 for accommodating a stoma 20, and a peripheral portion 100 circumferencing the central portion 90. A release layer 110 is provided between the first adhesive layer 40 and the second adhesive layer 130, the location of the release layer 110 is here indicated by broken lines as the release layer is integrated in the wafer by being embedded in adhesive. The release layer 110 is in the form of multiple separate envelopes extending radially from the hole 60. If the hole 60 is cut to adapt the size of it, the envelopes will still be present at the edge portion of the hole.

Figure 5:
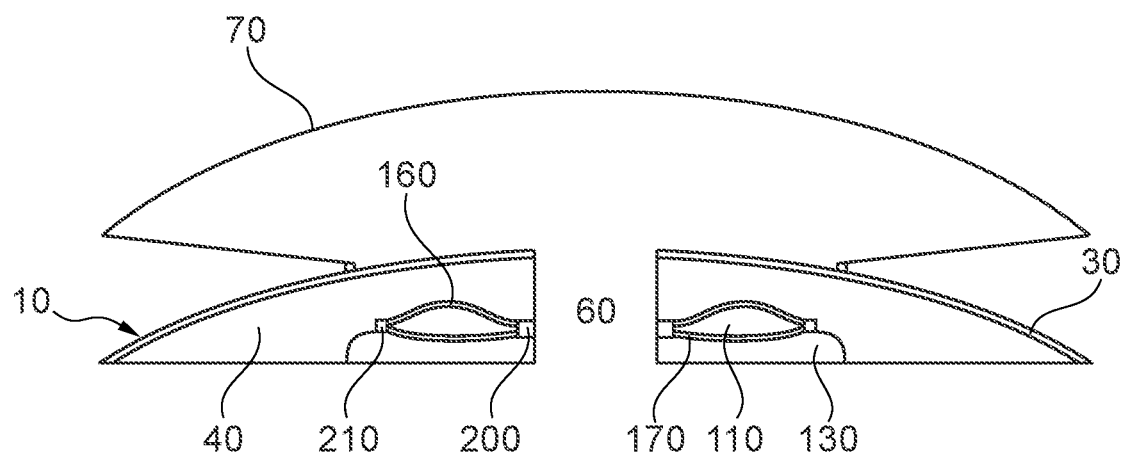
FIG. 5 illustrates a schematic cross-section view of an embodiment of a wafer.

FIG. 5 shows a cross-sectional view of an ostomy appliance. The appliance comprises an adhesive wafer 10 having a first layer of adhesive 40 facing a backing layer 30 covering the distal surface of the first adhesive 40. A central hole 60 is provided in the wafer. The wafer is provided with a collecting bag 70. A release layer 110 is located between the first adhesive layer and the second adhesive layer and at a distance from the hole 60. The release layer is provided in envelope in the form of a cover 140 layer comprising an upper layer 160 and a lower layer 170, sealed along an outer periphery 210. In a part of the envelope extending from the edge of the hole 60 to the release layer 110 is a wicking layer 200 facilitating moisture to be transported to the release layer.

Example

In a solution of PEG is suspended 1% particles of Protagold potato protein. The dispersion is provided in a 1 mm thick layer with the shape of a disc, and wrapped in a polyurethane film and sealed along the outer periphery of the disc to define a closed envelope. The envelope is placed on the central portion of a backing layer coated with a first adhesive layer and then a second adhesive layer is applied over the release layer, the second adhesive layer being larger than the envelope in order to embed the envelope with the release layer entirely in adhesive. A central hole is cut in the final laminate.

The used adhesive may be any suitable skin-friendly adhesive, a suitable example of an adhesive composition could comprise 50% w/w polyisobutylene (PIB) and 25% w/w CMC and 25% w/w pectin.

The invention claimed is:

1. An adhesive ostomy wafer attachable around a stoma of a user, where the adhesive ostomy wafer is adapted to secure a waste collecting device to the user to collect waste from the stoma, the adhesive ostomy wafer comprising:
 a backing layer that is gas and water impermeable;
 a first adhesive deposited onto a proximal side of the backing layer;
 a skin-facing adhesive located proximal of the first adhesive and adapted to adhere the adhesive ostomy wafer to skin around the stoma of the user; and
 a neutralizer contained by the adhesive ostomy wafer between the first adhesive and the skin-facing adhesive, where the neutralizer is one of a clay, a potato-derived inhibitor, and a protease inhibitor;
 wherein the adhesive ostomy wafer includes a stoma-receiving hole formed through the backing layer, the first adhesive, and the skin-facing adhesive, with the first adhesive and the skin-facing adhesive exposed within the stoma-receiving hole;
 wherein the neutralizer is contained within an envelope.

2. The adhesive ostomy wafer of claim 1, wherein the neutralizer comprises a wicking layer that is in contact with the neutralizer, with a portion of the wicking layer exposed within the stoma-receiving hole.

3. The adhesive ostomy wafer of claim 1, wherein the envelope is contained by the adhesive ostomy wafer between the first adhesive and the skin-facing adhesive, with the envelope extending to an edge of the stoma-receiving hole.

4. The adhesive ostomy wafer of claim 1, wherein the envelope surrounds the stoma-receiving hole.

5. The adhesive ostomy wafer of claim 1, wherein the neutralizer is contained within a plurality of envelopes, and the plurality of envelopes surround the stoma-receiving hole.

6. The adhesive ostomy wafer of claim 1, wherein the envelope comprises a distal layer separating the neutralizer from the first adhesive, a proximal layer separating the neutralizer from the skin-facing adhesive, with the distal layer sealed to the proximal layer at a location spaced away from the stoma-receiving hole such that the neutralizer is exposed within the stoma-receiving hole and contained between the distal layer and the proximal layer of the envelope.

7. The adhesive ostomy wafer of claim 1, further comprising a cover layer that prevents contact of the neutralizer with the first adhesive and the skin-facing adhesive.

8. The adhesive ostomy wafer of claim 1, wherein the neutralizer is contained within a matrix selected from the group consisting of a gel, a foam, a film, a paper.

9. The adhesive ostomy wafer of claim 1, wherein the neutralizer is contained within a water soluble matrix.

10. The adhesive ostomy wafer of claim 1, wherein the neutralizer is contained within a matrix that is adapted to absorb output from the stoma and form a gel.

11. The adhesive ostomy wafer of claim 1, wherein the neutralizer is contained within a matrix, and the matrix comprises a protein.

12. The adhesive ostomy wafer of claim 1, wherein the neutralizer is contained within a matrix, and the matrix is substantially non-adhesive.

13. The adhesive ostomy wafer of claim 1, wherein the neutralizer is contained within a matrix, and the matrix comprises a polysaccharide.

14. The adhesive ostomy wafer of claim 1, wherein the first adhesive is deposited onto an entirety of a proximal side of the backing layer, with the skin-facing adhesive deposited around the stoma-receiving hole onto less than an entirety of the first adhesive.

15. The adhesive ostomy wafer of claim 1, wherein the stoma-receiving hole is adapted to be tailor fit to anatomy of the stoma of the user by cutting layers of the adhesive ostomy wafer, and cutting the layers of the adhesive ostomy wafer exposes the neutralizer within the stoma-receiving hole.

16. The adhesive ostomy wafer of claim 1, wherein the waste collecting device is inseparably connected to a distal side of the backing layer.

17. An adhesive ostomy wafer attachable around a stoma of a user, where the adhesive ostomy wafer is adapted to secure a waste collecting device to the user to collect waste from the stoma, the adhesive ostomy wafer comprising:
   a backing layer that is gas and water impermeable;
   a first adhesive deposited onto a proximal side of the backing layer;
   a skin-facing adhesive located proximal of the first adhesive and adapted to adhere the adhesive ostomy wafer to skin around the stoma of the user; and
   a neutralizer contained by the adhesive ostomy wafer between the first adhesive and the skin-facing adhesive, where the neutralizer is one of a clay, a potato-derived inhibitor, and a protease inhibitor;
   wherein the adhesive ostomy wafer includes a stoma-receiving hole formed through the backing layer, the first adhesive, and the skin-facing adhesive, with the first adhesive and the skin-facing adhesive exposed within the stoma-receiving hole;
   wherein the neutralizer is contained within a cover layer that prevents contact of the neutralizer with the first adhesive and the skin-facing adhesive, and the cover layer is segmented into zones located around the stoma-receiving hole, where the zones are adapted to maintain the neutralizer in a form-stable configuration when the neutralizer is exposed to output from the stoma.

18. An adhesive ostomy wafer attachable around a stoma of a user, where the adhesive ostomy wafer is adapted to secure a waste collecting device to the user to collect waste from the stoma, the adhesive ostomy wafer comprising:
   a backing layer that is gas and water impermeable;
   a first adhesive deposited onto a proximal side of the backing layer;
   a skin-facing adhesive located proximal of the first adhesive and adapted to adhere the adhesive ostomy wafer to skin around the stoma of the user; and
   a neutralizer contained by the adhesive ostomy wafer between the first adhesive and the skin-facing adhesive, where the neutralizer is one of a clay, a potato-derived inhibitor, and a protease inhibitor;
   wherein the adhesive ostomy wafer includes a stoma-receiving hole formed through the backing layer, the first adhesive, and the skin-facing adhesive, with the first adhesive and the skin-facing adhesive exposed within the stoma-receiving hole;
   wherein the neutralizer is contained within a cover layer that prevents contact of the neutralizer with the first adhesive and the skin-facing adhesive, with the cover layer is impermeable to moisture.

\* \* \* \* \*